United States Patent [19]

Kirsch

[11] Plant 4,646

[45] Feb. 10, 1981

[54] LILY PLANT NAMED SUPERSTAR

[75] Inventor: Ted T. Kirsch, Myrtle Point, Oreg.

[73] Assignee: Sun Valley Bulb Farms, Inc., Myrtle Point, Oreg.

[21] Appl. No.: 79,331

[22] Filed: Sep. 27, 1979

[51] Int. Cl.[3] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—Chas. W. Rummler

[57] ABSTRACT

A new and distinct variety of Oriental hybrid lily plant of the Parkmannis type, particularly distinguished by the glossy, purplish red coloring of its large, seven to eight inch diameter, slightly cupped, upwardly facing flowers which comprise a raceme inflorescence borne on long, strong stems and having strong, erect pedicels, each pedicel usually having one bud or flower. This new plant is also distinguished by its habit of blooming profusely in July and by its dark green, glossy and relatively disease resistant foliage.

2 Drawing Figures

BACKGROUND OF THE NEW PLANT

This new variety of lily plant was discovered by me as a seedling of unknown parentage growing at my nursery in Arcata, Calif. The brilliantly colored, upwardly facing flowers and its dark green, glossy foliage, which was observed to be relatively disease resistant, prompted me to propagate this new plant for testing of its adaptability for commercial use. Continued propagation of this new lily through successive generations by means of scales and by tissue culture at Arcata, Calif., has demonstrated that the new plant has advantageous and distinctive characteristics which would make it a valuable addition to the field of commercial lily culture for use as a garden flower and for cut flower production. Successive generations of this new plant by asexual propagation have demonstrated that its distinctive characteristics hold true from generation to generation and appear to be firmly fixed.

DESCRIPTION OF THE DRAWINGS

This new variety of lily plant is illustrated by the accompanying full color photographic drawings, of which

DESCRIPTION OF THE NEW PLANT

Figure 2:
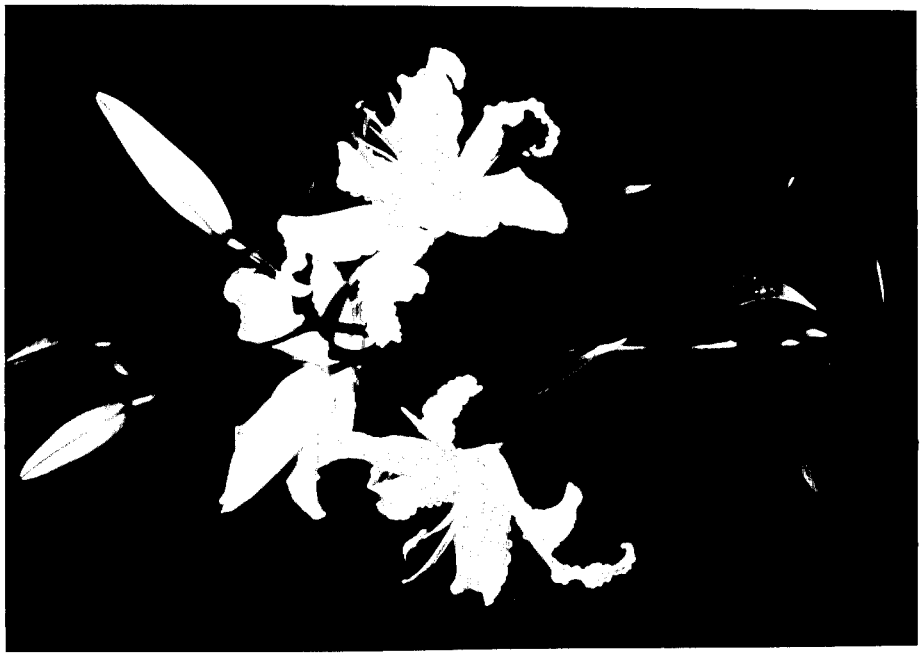
FIG. 1 is a face view of a fully opened flower and FIG. 2 is a view showing a blooming pot plant arising from a rather small bulb and bearing several buds in various stages of growth.
Figure 1:
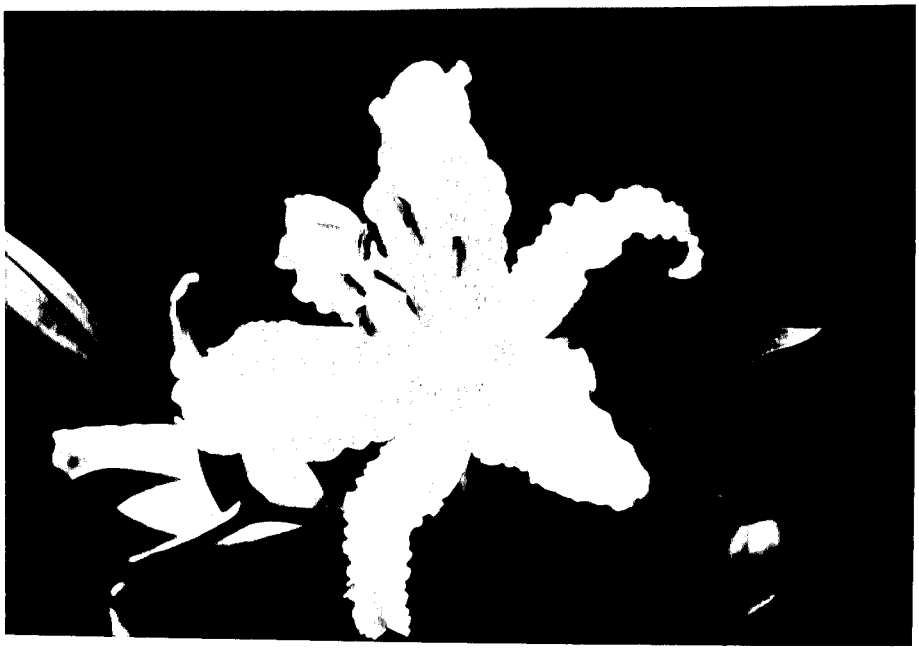

The following is a detailed description of my new variety of lily as observed at Arcata, Calif., the color designations being according to The Royal R.H.S. Colour Chart published by The Royal Horticultural Society of London, England.

THE PLANT

Origin: Seedling.
Parentage: Unknown.
Classification:
- *Botanic.*—Oriental Hybrid, Parkmannis Type.
- *Commercial.*—Lily plant for garden culture and cut flower production.

Form: A tall, single stem arising from each bulb.
Height: 3 to 5 feet at maturity.
Growth: Upright, sturdy and with excellent strength.

Cane size: Stems have a diameter of about $\frac{1}{4}$ inch at a height of 2 feet and grow to about $\frac{3}{4}$ inch diameter at a height of about 4 feet.
Foliage: Quantity—Abundant.
- *Leaves at flower cluster.*—2 in number; 1 at the base of each pedicel about $5\frac{1}{2}$ inches long and 2 inches wide; and 1 on the pedicel about 1 inch from the flower bud and having a length of about 4 inches and a width of about 1 inch.
- *Shape of leaf.*—Lanceolate.
- *Texture.*—Leathery.
- *Aspect.*—Smooth and glossy.
- *Ribs and veins.*—Distinct longitudinal veins from base to tip.

Stem bulblets (under ground):
- *Occurrence.*—1 to 3 on each healthy, normal plant at digging time.
- *Size.*—From about $\frac{1}{4}$ inch to 1 inch in diameter.
- *Color.*—White with occasional pink shading at the tips.

Bulbs:
- *Size.*—From $\frac{1}{4}$ inch to 12 inches in circumference depending upon age.
- *Color.*—White, with yellow and pink overtones. As bulbs become larger and older, the overtones of yellow and pink become more and more prominent.

THE BUD

Form: Lanceolate with acuminate apex.
Size: Average about 4 inches to 6 inches long and 1 inch to $1\frac{1}{2}$ inches in diameter.
Number: Usually 1 on each pedicel, with 1 to 15 buds on the plant stem according to culture and bulb size.
Opening rate: Normal, the buds opening successively from the lowermost bud to the terminal bud, which is the last to open.
Color: Whitish pink at the tip of the bud and deepening to a darker pink at the base of the bud when the sepals first divide and petals begin to unfurl.
Surface texture: Leathery and rugose with prominent veins.
Pedicel: Strong and generally straight, angled upward about 75° from the vertical; Glabrous with a light green color on the under side and dark maroon on the top.

*Length.*—From about 2½ inches to 3 inches.

THE FLOWER

Blooming habit: Annually, blooming profusely in July.

Size of flower: Large, averaging 7 to 8 inches in diameter.

Borne: From larger bulbs, the inflorescence has a raceme arrangement with each pedicel bearing 1 bud. The size of the bulb and its cultural care will determine the number of blooms and buds to be found in any particular inflorescence. From large bulbs, this lily may have 4 to 8 blooms open at one time.

Shape: Slightly cupped with uniformly spaced petals in star arrangement, with the very tips of the petals folding and curving backwardly.

Petalage: Normal, with 3 sepals and 3 petals.

*Form.*—Oval, with cuspidate apex and prominent nectariferous grooves with a center furrow bisecting each petal longitudinally. The edges of both sepals and petals are sinuate and each has a length of about 5 inches and width of about 2½ inches.

Color (when grown outside, on the west coast of the United States):

*Upper side.*—Upon opening, the center of each petal and sepal is Red Purple RHS 60B which fades to RHS 60C toward the tip, each having an undulated or frilled White margin, RHS 155D, about ⅛ inch to ¼ inch wide. The frilling is somewhat more pronounced on the sepals than on the petals. The base of the petals is White, RHS 155D, and with the exception of 1½ inches of the tip and the White margins, the entire area of the petals is profusely covered with very dark, prominent, oblong spots.

*Under side.*—Mainly RHS 70C with White margins of RHS 155D.

*Texture.*—Leathery.

*Aspect.*—Velvety.

*Papillae.*—From 4 to 8 in number and present on each of the petals.

*Fragrance.*—Sweet.

Discoloration: The color darkens somewhat as the bloom matures.

Persistence: The flower tends to hang on and dry.

Effect of weather: Generally the flower is not affected by wet weather but the flower ages more rapidly as the temperature rises.

Lasting quality:

*On the plant.*—2 to 3 weeks, depending upon the size of the bulb and environmental temperature.

*As a cut flower.*—10 days to 2 weeks.

REPRODUCTIVE ORGANS

Stamens: Number — Six.

*Anthers.*—Length — About 1 inch. Arrangement: Orderly, around the pistil.

*Filaments.*—Length — About 2½ inches. Color: Greenish Yellow.

Pistils: Number — One.

*Style.*—Length — About 3¼ inches. Color: Light Green at the base darkening somewhat at the stigma.

*Stigma.*—Color — Purple Gray.

Ovary: Classified as a schizocarp, about 3½ to 4 inches long and about 1½ inches in diameter, dehiscing into thirds and containing 6 rows of seeds of the usual shape for lilies.

This new lily plant most nearly resembles the variety "Star Gazer" (U.S. Plant Pat. No. 4,085) and the following table shows a comparison of the pertinent details of the two lily plants:

| | SuperStar | Star Gazer |
|---|---|---|
| A Blossom | | |
| 1. Form: | Flat, when fully opened. | Slightly cupped, when fully opened. |
| 2. Color: | Red Purple group center - 60B shading to 60C | Red group center - 64B shading to 64D |
| 3. Petals: | | |
| A. Arrangement: | More space between petals. | Less space between petals. |
| B. Shape: | Edges roll under full length of petal; ruffled more than Star Gazer. | Edges roll in; ruffled less than SuperStar. |
| B. Flowering | | |
| 1. Response: | Blooms earlier than Star Gazer. | Blooms later than SuperStar. |
| C. Plant | | |
| 1. Height: | 3 to 5 feet depending on age of bulb. | 2 to 4 feet depending on age of bulb. |
| 2. Pedicels: | Upfacing with a tendency to turn outwards. | Acutely upright. |

I claim:

1. A new and distinct variety of Oriental hybrid lily plant, substantially as herein shown and described, characterized by its very large, upwardly facing flowers borne on strong, stiff pedicels, and by the substantially overall bright purplish red coloring of the sepals and petals which are bordered by a white sinuous margin.

* * * * *